United States Patent [19]

Masurekar et al.

[11] 4,072,568
[45] Feb. 7, 1978

[54] METHOD FOR THE PREPARATION OF CHOLESTEROL OXIDASE

[75] Inventors: Prakash S. Masurekar, Webster; Charles T. Goodhue, Rochester, both of N.Y.

[73] Assignee: Eastman Kodak Company, Rochester, N.Y.

[21] Appl. No.: 739,379

[22] Filed: Nov. 5, 1976

Related U.S. Application Data

[62] Division of Ser. No. 629,955, Nov. 7, 1975, Pat. No. 4,035,237.

[51] Int. Cl.$^2$ .............................................. C12D 13/10
[52] U.S. Cl. ....................................................... 195/65
[58] Field of Search ................................. 195/66 R, 65

[56] References Cited

U.S. PATENT DOCUMENTS 3,909,359  9/1975  Goodhue ........................... 195/66 R

OTHER PUBLICATIONS

Merk Index, Eighth Ed., p. 951, (1968).

Primary Examiner—Alvin E. Tanenholtz
Attorney, Agent, or Firm—Arthur L. Girard

[57] ABSTRACT

A method for preparing cholesterol oxidase, comprising the steps of:
  a. growing a cholesterol oxidase producing microorganism in a medium comprising a nontoxic concentration of nonionic surfactant to yield extracellular cholesterol oxidase; and
  b. separating the extracellular cholesterol oxidase from the medium.

Preferably, cholesterol oxidase is prepared from a growth medium of *Nocardia cholesterolicum* species NRRL 5767 or 5768 which contains cholesterol, a suitable derivative of cholesterol or a 3-$\beta$-hydroxy sterol as a cholesterol oxidase inducer and a nonionic surfactant in a concentration which is not toxic to said bacterium, which does not produce decomposition products in concentrations sufficient to be toxic to said bacterium, and in sufficient concentration to produce extracellular enzyme.

2 Claims, 2 Drawing Figures

METHOD FOR THE PREPARATION OF CHOLESTEROL OXIDASE

This is a division of application Ser. No. 629,955, filed Nov. 7, 1975, now U.S. Pat. No. 4,035,237.

FIELD OF THE INVENTION

The present invention relates to an improved method for the synthesis of cholesterol oxidase and more particularly to an improved method for the synthesis of extracellular cholesterol oxidase.

BACKGROUND OF THE INVENTION

Microorganisms capable of metabolizing cholesterol are potential sources of enzymes useful in an enzymatic assay of cholesterol is complex mixtures such as blood serum, etc. This is particularly so if the microorganisms can use cholesterol as a sole carbon source, for in this assay process cholesterol must be degraded by oxidative enzymes.

Stadtman, T. C., Methods in Enzymology, Vol. 1, Colowick, S. P. and Kaplan, N. O., Eds. Academic Press, N.Y. 1955, P. 678 and Stadtman, T. C., Cherkes, A. and Anfinsen, J., Biol. Chem., 206, 510 (1954) reported the preliminary purification of an enzyme from Nocardia cholesterolicum, an organism originally isolated by Schatz et al (Schatz, A., Savard, K., and Pintner, I. J., J. Bacteriol., 58, 117–125 (1949). Stadtman's enzyme, "cholesterol dehydrogenase," was purified sufficiently for use in a cholesterol assay based on the measurement of the increase in absorbance at 250 nm owing to the formation of cholest-4-en-3-one. Since as we have now determined, the direct acceptor of cholesterol electrons in this oxidation is oxygen, the enzyme should properly be called cholesterol oxidase according to current convention.

The bacterial strains described by Stadtman when cultured as described in the aforementioned references produce very low enzyme levels which are not practical for commercial operations. These levels are sufficiently low that purification of the enzyme is a very remote possibility for achieving a commercial operation.

Goodhue et al in U.S. Pat. No. 3,909,359 issued Sept. 30, 1975, describe an improved method for the production of the Stadtman cholesterol oxidase which comprises the steps of:

a. growing the bacterium Nocardia cholesterolicum species NRRL 5767 or NRRL 5768 in a medium in which cholesterol or a suitable derivative thereof serves as an auxiliary source of carbon; and b. isolating from said medium a cell-free extract containing the active enzyme.

Although the method described in this application is greatly improved over the original synthesis described by Stadtman and can be said to render the process commercially practical, it still poses a shortcoming in that the enzyme is produced predominantly intracellularly. For this reason actual extraction of the enzyme from the growth medium requires the use of time-consuming, expensive cell disruption techniques such as homogenization, etc.

German OLS 2,246,695 published Mar. 29, 1973, describes a method of isolating a cholesterol oxidase enzyme produced by a culture of Nocardia microorganism identified as NRRL 5635 and NRRL 5636. According to the method described therein, the harvested cells are treated with a nonionic surfactant and stirring at room temperature to release a large proportion of the enzyme from the cells into the supernatant thereby eliminating the need for involved cell extraction and isolation techniques. Using this technique for enzyme extraction we have calculated that yields on the order of about 40 to 160 U per liter are obtined.

Reese, E. T. and Maquire, A., in Surfactants as Stimulants of Enzyme Production by Microorganisms, Applied Microbiology, February, 1969, P. 242 – 245 describe the observation that the addition of sorbitan polyoxyethylene monooleate (Tween 80 from Atlas Chemical Co., Wilmington, Delaware) and other nonionic surfactants to fungal cultures which normally produce extracellular enzymes, results in a marked increase in enzyme yield.

British Pat. No. 1,385,319 describes a process for producing cholesterol oxidase from Nocardia species NRRL 5635 and NRRL 5636. During the fermentation, a suspension of cholesterol is slowly added as an inducer for cholesterol oxidase. A non-ionic surfactant, Tween 80, at a level of 3% by volume is used to disperse the cholesterol in the suspension. This results in only a minute amount of non-ionic surfactant in the fermentation medium, which amount is apparently insufficient to produce extracellular enzyme.

The bacterial cultures known to produce cholesterol oxidase, normally produce the enzyme intracellularly. The present invention provides an improved method for the production of cholesterol oxidase, wherein the enzyme is produced extracellularly thereby eliminating the need for cell disruption.

SUMMARY OF THE INVENTION

Attainment of the foregoing result and other advantages which will become apparent in the discussion which follows are obtained by including in the growth medium a nonionic surfactant in a concentration which is itself nontoxic and whose decomposition products are not in sufficient concentration to be toxic to the cholesterol oxidase-producing organism. The inclusion of this ingredient results in the majority of the enzyme being produced extracellularly. Thus, substantial reduction in the time and cost incident to enzyme extraction after production are achieved by eliminating the need for cell disruption which is generally required when the enzyme is produced intracellularly.

DETAILED DESCRIPTION OF THE INVENTION

Figure 2:
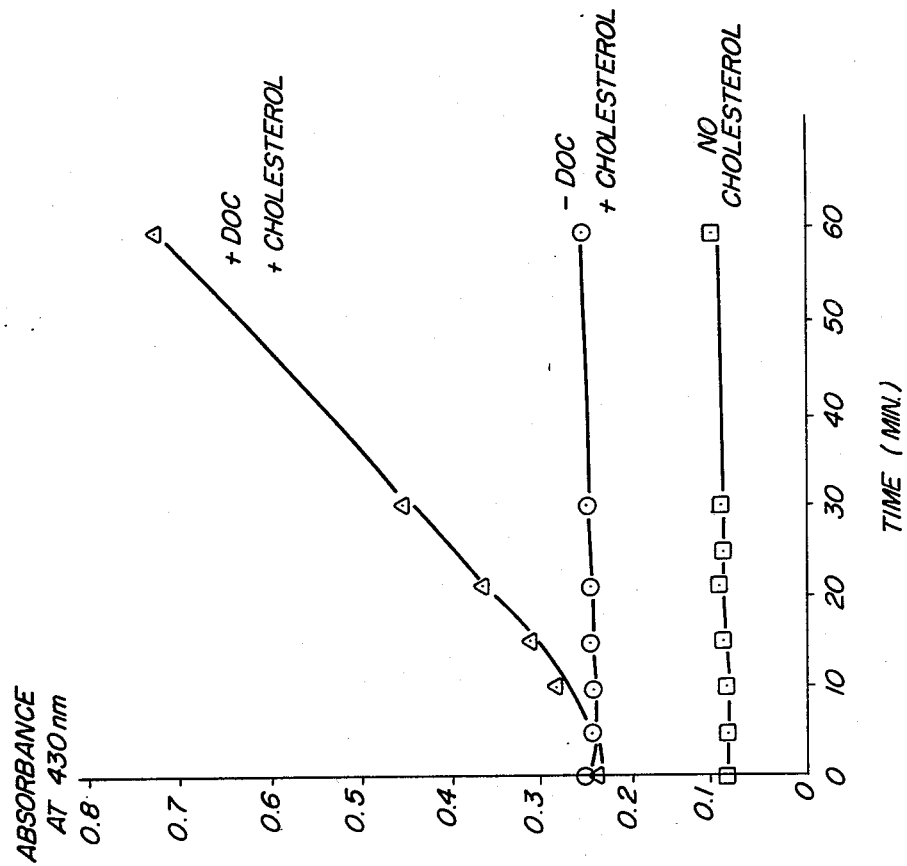
FIG. 2 illustrates the relationship between cholesterol oxidase activity and the presence of cholesterol and deoxycholate (DOC).

According to the present invention principally extracellular cholesterol oxidase production is achieved when a nonionic surfactant which is itself not toxic and whose decomposition products are nontoxic to the microorganism is added to a growth medium which produces cholesterol oxidase. Preferably, the bacterium, Nocardia cholesterolicum species NRRL 5767 or NRRL 5768, is grown in a medium comprising cholesterol, a suitable derivative thereof, or a 3-β-hydroxy sterol as an inducer of cholesterol oxidase.

According to a preferred embodiment, the nonionic surfactant has a polyoxyethylene or polyglycidol hydrophilic moiety and a lipophilic moiety comprising at least nine carbon atoms. According to a further preferred embodiment, the lipophilic moiety comprises a fatty acid chain of at least ten carbon atoms.

Any culture which produces cholesterol oxidase can be used in the practice of this invention. Cultures known to produce cholesterol oxidase include, for example, *Arthobacter crystallopoities*, *Arthobacter* strain NP, *Corynebacterium* species, *Mycobacterium* strain MA-7, *Mycobacterium* strain E-16, *Mycobacterium rhodochrous*, or other species from so-called *Mycobacterium rhodochrous* group, *Mycobacterium rubrum*, *Nocardia erythropolis*, *Nocardia* species NRRL 5635 and 5636, *Nocardia cholesterolicum* — smooth and *Nocardia cholesterolicum* — rough.

Two *Nocardia cholesterolicum* cultures which yield cholesterol oxidase and are especially preferred in the practice of the present invention are characterized as the "rough" and "smooth" strains and are called NRRL 5767 and NRRL 5768 respectively based on their deposit with the Agricultural Collection Investigations Fermentation Laboratory, Peoria, Illinois.

Complete details of the organisms are as follows:

Description of *Nocardia cholesterolicum*

I. Cellular morphology.

A. Smooth strain. Gram positive weakly acid-fast, coryneform, no well-developed mycelia, but rudimentary branching observed. Coccoid forms appear in older cultures.

B. Rough strain. Same as above.

II. Colonial morphology.

A. Nutrient agar (5 days, 30° C).
1. Smooth strain. circular, convex, watery, entire, smooth, glistening, pink-white. No soluble pigment.
2. Rough strain. circular, convex, entire, smooth to rough, pink-white. No soluble pigment.

B. Yeast glucose agar (5 days, 30° C).
1. Smooth strain. cream to tan-colored, watery, smooth, round, and elevated.
2. Rough strain. dry, cream to tan-colored, round, and elevated.

C. Casein agar (5 days, 30° C).
1. Smooth strain. cream to tan-colored, watery, round, smooth, elevated.
2. Rough colony. Tan to pink, dry, elevated.

D. Gelatin agar.
1. Smooth strain. circular, convex, entire, smooth, watery, cream-colored.
2. Rough strain. circular, convex, entire, dry, cream-colored.

III. Growth in liquid culture (Nutrient broth, 5 days, 30° C).

A. Smooth strain. off-white to tan flock-forming precipitate, no pellicle.

B. Rough strain. off-white to tan flock-forming precipitate, no pellicle.

| IV. Physiology (Smooth and Rough strains identical) | |
|---|---|
| Aeration | aerobic |
| Gelatin hydrolysis | − |
| Casein hydrolysis | − |
| Starch hydrolysis | − |
| *-continued* | |
| Oxidase | − |
| Catalase | + |
| Urease | − |
| Indole | − |
| Methyl red | − |
| Phenylalanine deamination | − |
| Litmus milk | alkaline |
| Use of compounds as sole carbon source | |
| Citrate | + |
| Lactate | + |
| Malate | + |
| Succinate | + |
| Fructose | + |
| Glucose | + |
| Sucrose | ± |
| Maltose | + |
| Glycerol | + |
| Sorbitol | + |
| Trehalose | + |
| Raffinose | − |
| Dulcitol | − |
| Lactose | − |
| Mannitol | + |
| Starch | − |
| Arabinose | − |

According to the method described in Goodhue et al, which produced intracellular cholesterol oxidase, the use of a conventional primary carbon source such as glycerol, in combination with a secondary or auxiliary carbon source such as cholesterol, cholest-4-en-3-one, or cholesteryl linoleate, all of which act as cholesterol oxidase inducers, increases the yield of cholesterol oxidase enzyme to levels about 100 times higher than those produced when cholesterol oxidase inducer is not used or when cholesterol is used as the sole carbon source as described in the prior art.

Thus, according to Goodhue improved yields were obtained when the bacterium was grown in a conventional nutrient medium of the type well known in the art which generally comprises a nitrogen source such as ammonium sulfate, a potassium and a phosphorus source such as potassium phosphate, trace metal ions, and a mixture of a primary carbon source such as glycerol and a cholesterol oxidase inducer selected from the group consisting of cholesterol, cholest-4-en-3-one, cholesteryl linoleate, and mixtures thereof. The pH value of the medium is maintained between about 5.0 and 8.0, preferably between about 6.5 and 7.5, at a temperature of from about 18 to about 35° C, preferably about 25°–30° C, for a period of from about 18 to about 40 hours, preferably from about 20 to about 24 hours.

The quantities of nitrogen, potassium phosphate and trace metal ions used in the culture are those conventionally used in processes of this type and are well known to those skilled in the art. Specifically, those described in the aforementioned references provide useful levels of these constituents.

Among the primary carbon sources which were found useful by Goodhue et al and which are similarly useful herein are glycerol, glucose, and acetic acid. Conventional concentrations of primary carbon source are used. These generally range from about 0.5% to about 5% by weight. The concentration of the cholesterol oxidase inducer utilized, generally ranges from about 0.05% to about 0.5% by weight. A preferred range of inducer is from about 0.1% to about 0.2% by weight.

According to the improved process described herein, cholesterol oxidase is prepared substantially as described by Goodhue et al except that the growth medium further includes a non-inhibiting concentration of a nonionic surfactant which is not toxic to the microorganism and whose decomposition products are similarly nontoxic as described hereinafter. Inclusion of such a material in the fermentation medium results in the production of primarily extracellular cholesterol oxidase which eliminates the necessity for time-consuming, complicated and costly cell harvesting extraction techniques of the sort used in the prior art.

Any nonionic surfactant which meets the aforementioned criteria is useful in the successful practice of the instant invention.

Nonionic surfactants are well known in the art and no further definition thereof is required herein. Typical examples of such materials include polyethylene glycol, polyvinyl alcohol, polyethers, polyesters, and polyhalides.

Of critical importance to the successful practice of the invention are the criteria that 1. neither the particular nonionic surfactant used nor its decomposition products are toxic to the microorganism in the concentrations required to produce extracellular enzyme; and 2. the amount of surfactant used does not inhibit enzyme production.

Surfactant toxicity for the microorganism can, of course, be determined readily by subjecting a culture of the microorganism to a relatively low concentration of the surfactant, on the order of about 0.5 g/l, and observing the effect of such a treatment on the microorganism. Inhibition of growth of the microorganism will generally result in zones of retarded growth of the culture in a petri plate where contact with a toxic material occurred.

The toxicity of the decomposition products of the surfactant can be theorized as described briefly hereinafter, however, the only positive test for such a criterion is evaluation in the growth medium and observation of the effects of by-products produced therein as shown in the examples below.

Although the inventors do not wish to in any way be limited to a specific theory for the mechanism of the successful practice of their invention, it appears that, as demonstrated in the examples below, nonionic surfactants which are known to decompose into toxic moieties, e.g., into phenols, are not useful in the successful practice of the invention.

Useful nonionic surfactants include a broad range of materials and any such material which meets the two criteria described hereinabove are useful in the successful practice of the invention.

According to a preferred embodiment wherein cholesterol oxidase is prepared as described hereinabove the nonionic surfactant has a polyoxyethylene or polyglycidol hydrophilic moiety and a lipophilic moiety comprising at least nine carbon atoms. According to a highly preferred embodiment the lipophilic moiety comprises a fatty acid chain of at least ten carbon atoms.

Optimum results are achieved when the fatty acid chain contains at least 16 carbon atoms and the hydrophilic moiety comprises about 20 polyoxyethylene units.

The following is a list of specific surfactants found particularly useful in the successful practice of the instant invention and their structure:

| Surfactant | Hydrophile | No. of Units | Lipophile | No. of Units |
|---|---|---|---|---|
| S-1 | Sorbitan | 1 | Lauric acid | 1 |
| S-2 | Polyoxyethylene Sorbitan | 20 1 | Lauric acid | 1 |
| S-3 | Polyoxyethylene Sorbitan | 4 1 | Palmitic acid | 1 |
| S-4 | Polyoxyethylene Sorbitan | 20 1 | Stearic acid | 1 |
| S-5 | Polyoxyethylene Sorbitan | 20 1 | Stearic acid | 1 |
| S-6 | Polyoxyethylene Sorbitan | 4 1 | Stearic acid | 3 |
| S-7 | Polyoxyethylene Sorbitan | 20 1 | Oleic acid | 1 |
| S-8 | Polyoxyethylene Sorbitan | 20 1 | Oleic acid | 1 |
| S-9 | Polyoxyethylene | 5 | Nonylphenyl | 1 |
| S-10 | Polyoxyethylene | 10 | Nonylphenyl | 1 |
| S-11 | Polyoxyethylene | 15 | Nonylphenyl | 1 |
| S-12 | Polyglycidol | 30 6 | Nonylphenyl | 1 |
| S-13 | Polyglycidol | 10 | Nonylphenyl | 1 |

Among the nonionic surfactants which were not found useful in the successful practice of the invention were the octylphenyl polyethoxy ethanols commercially available from Rohm and Haas of Philadelphia, Pa., under the Triton trademark. It is theorized that such materials produced toxic phenols upon decomposition and that they were therefore unsatisfactory. S-14 (Triton-X-100) which is of this class and comprises 9.5 polyethoxyethylene units and 1 octylphenyl unit is evaluated in the Examples below.

Specific examples of each class of the foregoing compounds, their relative effectiveness in releasing cholesterol oxidase, commercially available materials of this type and optimum concentrations are demonstrated and defined in the examples which follow.

The concentration of nonionic surfactant used in any particular growth medium will vary considerably depending upon the composition of the medium, the sensitivity of the medium to the particular surfactant and the particular surfactant used. Generally, however, surfactant concentration ranges of from about 0.5 to about 10.0 g/liter of medium have been found useful in at least certain fermentation media with certain surfactant compositions. At levels above 10 g/liter the surfactant generally acts as a growth inhibitor, most probably due to surfactant or surfactant by-product toxicity to the micro-organism. At levels below 0.5 g/liter no significant release of cholesterol oxidase is observed. It is generally preferred, as demonstrated by the extensive exemplary results set forth below, to utilize surfactant concentrations between about 1 and 5 g/liter of medium.

As described hereinabove, the growth medium includes a primary carbon source such as, for example, glycerol, reagent grade glucose, technical grade corn syrup, or the like, and an inducer of cholesterol oxidase which may also be an auxiliary carbon source. Besides the cholesterol, cholest-4-en-3-one and cholesteryl linoleate which were taught as inducers by Goodhue et al, supra, other sterols and cholesterol esters are useful as inducers of cholesterol oxidase. Other preferred inducers include, for example $\beta$-sitosterol and $5\alpha$-cholestan-3-$\beta$-ol, and cholesterol esters such as cholesteryl oleate, cholesterol linolenate, cholesteryl formate and cholesteryl propionate.

Any conventional nitrogen compound can be used as the nitrogen source in the growth medium. An especially preferred nitrogen source for the practice of the present invention is Nutrient Broth, a product of Difco Laboratories, Detroit, Michigan, containing peptone and beef extract. Other nitrogen sources found useful in the practice of this invention include, for example, Anatone, available from Cudahy Laboratories, Omaha, Nebraska, and N-Z/amine Type AT, N-Z/amine Type BT, N-Z/amine Type ET, N-Z/amine Type TT, Soy Petone Type T, Fermamine Type I, Fermamine Type II and Fermamine Type III, all available from Sheffield Chemical Div. of Kraftco Corp., Union, New Jersey.

In the production of cholsterol oxidase using a growth medium containing a nonionic surfactant in accordance with the teachings of this invention, foaming is often encountered. In order to control the foaming, especially when producing large batches, use of a foam control agent is advisable. One such foam control agent found useful in the practice of this invention is Polyglycol P-2000, available from Dow Chemical Co. (Midland, Michigan). Other foams control agents can also be used, the main criteria for selection and use being the lack of inhibition of enzyme synthesis at a concentration level which will control the foam.

In the following examples which are presented to better demonstrate the successful practice of the invention the following definitions apply:

1. Culture: unless otherwise stated the "rough strain" (NRRL 5768) of Nocardia cholesterolicum was used.

2. Nutrient Media

The compositions of media used in the Examples are as follows:

| a) | Glycerol medium | per liter |
|---|---|---|
| | Ammonium sulfate | 2.0 g |
| | Potassium phosphate (dibasic) | 2.0 g |
| | Salt solution "C" | 5.0 ml |
| | Glycerol | 5.0 g |
| | Tryptone | 0.1 g |
| | Cholesterol | 1.0 g |
| | Distilled water | to 1 liter |
| | Salt solution "C" | per liter of 0.1 N HCl |
| | Magnesium sulfate . 7H$_2$O | 25.0 g |
| | Calcium chloride . 2H$_2$O | 0.1 g |
| | Ferrous sulfate . 7H$_2$O | 2.8 g |
| | Manganese sulfate . H$_2$O | 1.7 g |
| | Zinc sulfate . 7H$_2$O | 0.06 g |
| | Sodium chloride | 0.6 g |
| b) | Modified glycerol medium | |
| | Same as (a) with | per liter |
| | Inositol | 1.0 g |
| | Yeast extract | 1.0 g |
| c) | Glucose medium | |
| | Same as (a) except glycerol is replaced with glucose. | |
| d) | S-3 medium | per liter |
| | Nutrient broth* | 8.0 g |
| | Yeast extract | 1.0 g |
| | Inositol | 1.0 g |
| | Cholesterol | 1.0 g |
| | S-3 | 5.0 g |
| | Distilled water | to 1 liter |
| e) | Yeast extract medium | per liter |
| | Yeast extract | 1.0 g |
| | Inositol | 1.0 g |
| | Sodium phosphate (dibasic) 7H$_2$O | 2.0 g |
| | Tryptone | 5.0 g |
| | Distilled water | to 1 liter |
| f) | Inoculum medium | per liter |
| | Glucose | 10.0 g |
| | Yeast extract | 10.0 g |
| | Potassium phosphate (dibasic) | 1.0 g |
| | Salt solution A-1 | 2.0 ml |
| | Salt solution A-2 | 2.0 ml |
| | Agar | 20.0 g |
| | Adjust pH to 7.0 and made up to 1 liter with distilled water. | |
| | Salt solution A-1 | per liter of 0.1 N HCl |
| | Magnesium sulfate . 7H$_2$O | 100.0 g |
| | Ferrous sulfate . 7H$_2$O | 10.0 g |
| | Manganese sulfate . 7H$_2$O | 1.0 g |

| | -continued | |
|---|---|---|
| | Sodium molybdate . 2H$_2$O | 0.5 g |
| | Made up to 1 liter with 0.1N hydrochloric acid. | |
| | Salt solution A-2 | |
| | | per liter |
| | Calcium chloride | 10.0 g |
| | Deionized distilled water | to 1 liter |
| g) | Modified S-3 medium | per liter |
| | Nutrient broth | 8.0 g |
| | Yeast extract | 1.5 g |
| | Cholesterol | 2.0 g |
| | S-3 | 5.0 g |
| | Polyglycol P-2000 | 0.3 g |

*A product of Difco Labs, (Detroit, Mich) containing peptone and beef extract.

3. Maintenance of the Culture

The cultures are maintained on the slants of glycerol medium containing cholesterol and are transferred every second day.

4. Preparation of Inoculum (Small Scale Use)

A slant of the inoculum medium (f) is inoculated with Nocardia cholesterolicum (rough) from a two-day-old glycerol medium slant and incubated at 30° C for 48 hours. The culture from this slant is removed with a wire loop and resuspended in 25 ml of sterile distilled water by vigorous shaking. The turbidity of the suspension is generally between 1.8 – 2.2 Optical Density (O.D.) units at 660 nm. Sixty ml of this suspension is used per liter of the medium to be inoculated.

5. Preparation of Inoculum for Large Scale Fermentation

Six 2.8 liter Fernbach flasks, each containing one liter of modified S-3 medium, are inoculated with 2-day-old culture of Nocardia cholesterolicum-rough grown on the slants of inoculum medium. The procedure used for this purpose is described above. One slant is used per flask. The flasks are shaken at 125 RPM and 30° C for 19 hours.

6. Fermentation

The fermentations are carried out in 2.8 liter Fernbach flasks and in 250 ml Erlenmeyer flasks. The volumes of medium used in the Fernbach flasks and Erlenmeyer flasks are 1 liter and 25 ml respectively. The medium in the flasks is inoculated as described above and incubated at 30° C. The shaker speed is adjusted to 125 RPM for the Fernbach flasks and to 200 RPM for the Erlenmeyer flasks. These medium volumes and the shaker speeds were selected because they resulted in similar rates of oxygen transfer. The samples are withdrawn aseptically every 24 hours for the meaurement of the cholesterol oxidase activity.

7. Harvesting the Cells

The cells are harvested (i.e., separated from the fermentation broth) by 15 minutes centrifugation in a refrigerated centrifuge (I. Sorvall Inc., Norwalk, Conn.) at 12,350 × g.

8. Determination of Cholesterol Oxidase Activity a. Preparation of cell fractions for the assay of cholesterol oxidase.

Cholesterol oxidase can be present outside the cell or extracellularly and inside the cell or intracellularly. Further, the intracellular enzyme can be present as free or soluble enzyme and as bound or insoluble enzyme. The extracellular enzyme can be assayed in the broth after the removal of the cells by centrifugation. To measure the intracellular enzyme the cells are disrupted by sonication.

The cell pellet obtained by centrifugation is suspended in 1 ml of distilled water and diluted to 20 ml with 50 mM potassium phosphate buffer (pH 7.0). It is sonicated for 5 minutes in an ice-water bath, in 1 minute bursts at 30 second intervals. The sonicated suspensions are centrifuged at 27,000 × g for 15 minutes in the cold. The activity in the supernatant is called the intracellular, soluble activity. The pellet is resuspended in 2% sodium deoxycholate and allowed to stand on ice for 10 minutes. It then is centrifuged at 27,000 × g for 15 minutes in the cold. The cholesterol oxidase activity in the supernatant is called the intracellular, insoluble activity. The sum of the extracellular, the intracellular soluble and the intracellular insoluble activities is called the total activity.

9. Enzyme Assay

Cholesterol oxidase activity is measured by the following technique:

Reagents:

a. 50 mM Potassium Phosphate buffer pH 7.0 (KP buffer): 30.5 ml 0.2 M $K_2H PO_4$ + 19.5 ml 0.2 M $KH_2PO4$ + water to 200 ml final volume.

b. 0.1% dianisidine solution: 10 mg 3,3'-Dimethoxybenzidine dihydrochloride per ml water. No pH adjustment.

c. Reagent Buffer: Add 0.4 ml dianisidine solution and 1.4 mg peroxidase powder (Sigma Type II, horseradish peroxidase, RZ 1.0 – 1.5 No. P8250) to 40 ml KP buffer, mix, dilute to 50 ml with KP buffer. The solution will turn turbid when the dianisidine is added but clears when mixed. This solution should be kept cold until ready to use. We have stored reagent buffer at 4° C for 3 days without problems, but routinely this reagent is prepared fresh daily.

d. Cholesterol solution: To 10 ml Triton X-100 (S-14) heated on a hot plate add 300 mg cholesterol powder and mix with stirring rod until solution clears. Add 90 ml water and stir. The solution will be cloudy, now continue mixing the flask by swirling it under a stream of cold water; the solution will become clear. Turbidity was due to detergent coming out of solution, the cooling rehydrates the detergent and fully solubilizes the steroid. This solution is stable for one week when stored at room temperature.

Reactions:

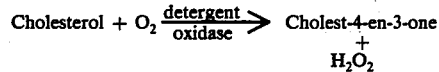

Assay:

a. 6.7 ml of reagent buffer plus 0.3 ml substrate are combined in a test tube, mixed, and placed in a waterbath set at 37° C. After five minutes 1.0 ml of enzyme solution is added to give 8 ml final volume in the tube and an initial reading at 430 nm on a Spectronic 20 spectrophotometer (Bausch and Lomb) is recorded. The tube is replaced in the waterbath. Tubes are read in the spectrophotometer every five minutes for 25 minutes. Rate of color development is determined from a plot of O.D. change vs. time, by averaging the O.D. change throughout the linear portion of the curve. Activity is calculated using a constant previously determined for the dye system from a standard curve. Enzyme preparations were diluted so that 0.005 to 0.06 units of cholesterol oxidase were used per assay tube.

b. For continuous assay of cholesterol oxidase a Beckman recording spectrophotometer is used. In this procedure 2.5 ml reagent buffer, 0.1 ml substrate and water are combined in a 3 ml cuvette. When temperature equilibration has occurred, enzyme is added and the rate of color development is followed at 430 nm. Incubation temperature is 37° C. Activity is calculated from the slope of the rate curve as described above. A convenient range of enzyme concentrations for this method is 0.001 to 0.02 units per cuvette.

One unit of cholesterol oxidase activity is that amount of enzyme catalyzing the production of 1 $\mu$ mole $H_2O_2$ per minute at 37° C and pH 7.0.

10. Determination of the Residual Cholesterol

Residual cholesterol is extracted from the fermentation broth and the cell suspension with a mixture of ethanol and n-heptane. Cholesterol in the organic phase is silanized and measured by gas chromatography.

The following examples serve to illustrate particular embodiments of the present invention. Unless otherwise indicated, concentrations given in percent are weight percent.

*Nocardia cholesterolicum* was grown in Fernbach flasks in the five different media described above under 2. Nutrient Media. The extracellular as well as the intracellular, insoluble cholesterol oxidase produced in each medium was measured and the results are reported in Table 1.

The amount of intracellular, insoluble cholesterol oxidase was about the same in the cells grown in the glycerol, glucose, and yeast extract media. The addition of inositol and yeast extract to the glycerol medium resulted in the inhibition of the enzyme production. There was no intracellular, insoluble cholesterol oxidase activity in the cells grown in S-3 medium. Unexpectedly, however, there was a significant amount of oxidase activity in the fermentation broth of this medium. In contrast, there was no extracellular activity in the broths obtained from the modified glycerol medium or from the yeast extract medium whereas those obtained from the glycerol medium or the glucose medium contained about 20 – 30% of the total cholesterol oxidase activity.

Figure 1:
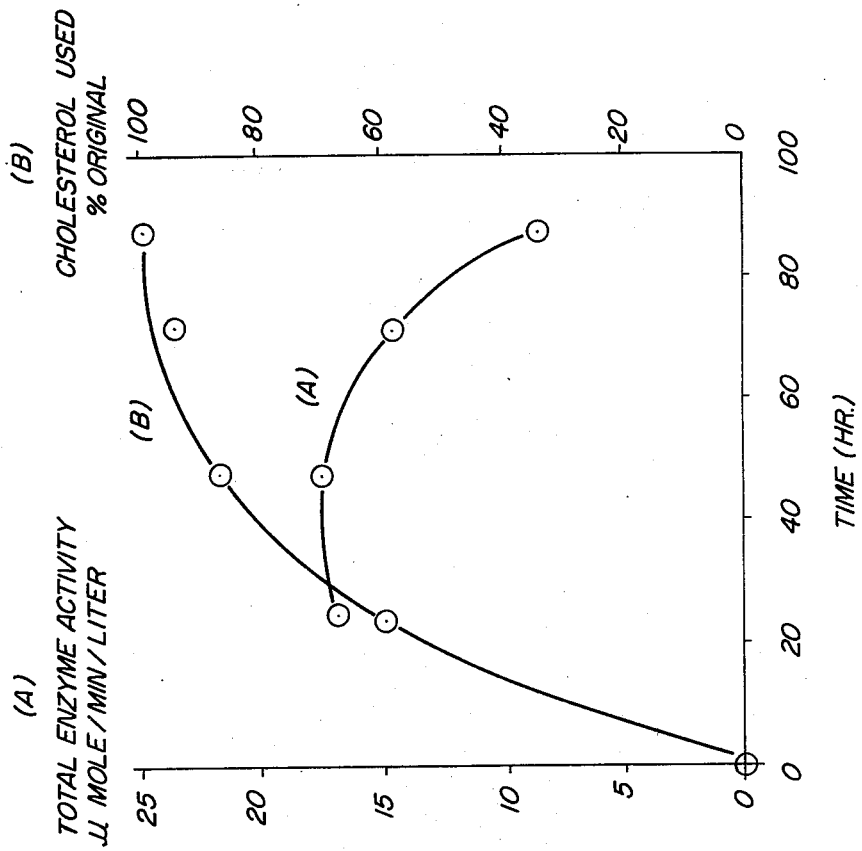
FIG. 1 illustrates cholesterol oxidase activity as a function of fermentation time and also the depletion of cholesterol in the fermentation medium with time.

Cholesterol oxidase produced by the cultures grown in the S-3 medium reached a maximum value of 17.5 international units (U) per liter (FIG. 1). This level is about 10 fold higher than that obtained with the glycerol medium. The amount of the extracellular enzyme decreased after 48 hours. The cultures were efficient utilizers of cholesterol (more than 90% of the cholesterol being used up in 3 days).

As the concentration of cholesterol in the medium diminished, the amount of the extracellular cholesterol oxidase decreased and the rate of cholesterol utilization fell.

Table I

Effect of Medium on the Production of Cholesterol Oxidase

| Medium | Cholesterol Oxidase U /Liter | | |
|---|---|---|---|
| | Intracellular insoluble | Extracellular | Total |
| Glycerol | 1.1 | 0.5 | 1.6 |
| Modified glycerol | 0.4 | 0 | 0.4 |
| Glucose | 1.1 | 0.3 | 1.4 |
| S-3 | 0 | 1.5 | 1.5 |
| Yeast extract | 1.5 | 0 | 1.5 |

Description of Cholesterol Oxidase

To show that the extracellular cholesterol oxidase was functionally the same as that extracted from the particulate fraction (i.e., the intracellular, insoluble fraction), its substrate specificity was qualitatively determined. As shown in Table 2, the extracellular enzyme did not exhibit any activity with either β-sitosterol or ergosterol. However, it did not act upon cholestanol. There was no activity in the absence of cholesterol or with boiled broth. In FIG. 2 it is seen that the extracellular cholesterol oxidase activity was dependent on cholesterol and deoxycholate (DOC) for its activity. All these characteristics are identical to those of the enzyme obtained by the detergent extraction of the particulate fraction (5).

These results indicate that medium was suitable for the production of cholesterol oxidase since the yields were 10 fold higher and the extracellular enzyme appeared to be functionally similar to the intracellular insoluble cholesterol oxidase.

Table 2
Partial Characterization of the Extracellular Cholesterol Oxidase

| Enzyme Source | Substrate | Activity* |
| --- | --- | --- |
| Unboiled broth | Cholesterol | + |
| Boiled broth | Cholesterol | − |
| Unboiled broth | Nothing added | − |
| Unboiled broth | β-Sitosterol | − |
| Unboiled broth | Ergosterol | − |
| Unboiled broth | Cholestanol | + |

*+ = Presence of activity
*− = Absence of activity

In the following examples unless otherwise noted the culture grown is *Nocardia cholesterolicum* - rough stain and the medium used is the S-3 medium described above.

EXAMPLE 2

Media similar to *Nutrient Media* 2. (d), above, but containing 0, 0.1, 0.5, 5, and 10 g of S-3 per liter of medium were prepared, inoculated and incubated in Fernbach flasks according to the general procedure given above. Each medium was assayed for cholesterol oxidase activity after 24, 48, and 72 hours incubation time. The results are contained in Table 3.

These results indicate that the increase in the production of cholesterol oxidase in S-3 medium is partly due to the richness of the medium and partly to the surfactant itself. For example, omission of S-3 from the medium decreased the production of the enzyme by 50%. It is seen in Table 3 that S-3 is useful in the production of extracellular oxidase in the range from 2 to 10 g/l of medium, preferably from 3 to 8 g/l. S-3 is particularly desirable at a level of 4 to 6 g/l.

Table 3

| Conc. of S-3 (g/l) | Time (hrs) | Intracellular Insoluble | Intracellular Soluble | Extracellular | Total |
| --- | --- | --- | --- | --- | --- |
| 0 | 24 | 3.8 | —* | 0 | 3.8 |
|  | 48 | 1.4 | 4.5 | 3.9 | 9.8 |
|  | 72 | 1.6 | 2.9 | 1.0 | 5.5 |
| 0.1 | 24 | 2.5 | —* | 0 | 2.5 |
|  | 48 | —* | —* | 4.1 | 4.1 |
|  | 72 | 2.1 | 2.2 | 1.3 | 5.6 |
| 0.5 | 24 | 2.6 | —* | 0 | 2.6 |
|  | 48 | 1.3 | 3.8 | 3.1 | 8.2 |
|  | 72 | 1.6 | 2.3 | 1.3 | 5.2 |
| 5.0 | 24 | 0.5 | —* | 0 | 0.5 |
|  | 48 | 1.3 | 3.1 | 17.2 | 21.6 |
|  | 72 | 1.4 | 1.8 | 14.0 | 17.2 |
| 10.0 | 24 | 0.2 | —* | 0 | 0.2 |
|  | 48 | 0 | 1.3 | 6.6 | 7.9 |
|  | 72 | 0 | 0.5 | 10.5 | 11.0 |

*Not assayed.

Site and Amount of Cholesterol Activity (U/l)*

EXAMPLE 3

Surfactants S-1, S-2, S-4, S-5, S-6, S-7 and S-8 were substituted for S-3 in the medium of Example 2 in a series of fermentations run in 250 ml Erlenmeyer flasks using 25 ml of the medium of Example 2 per flask. A flask containing S-3 as the surfactant was run concurrently as a control. The effects of three concentrations (0.5, 5.0 and 10.0 g/liter of medium) of each of the surfactants on the level of extracellular cholesterol oxidase at 24, 48 and 72 hours were tested.

The optimum concentration of each surfactant and the corresponding fermentation time for maximum production of extracellular cholesterol oxidase are noted in Table 4. All of the surfactants tested increased the production of extracellular oxidase. In general, a concentration of 5 g of detergent or less per liter was optimum for the production of the extracellular enzyme. With the exception of S-1, when the amount of surfactant was increased to 10 g per liter inhibition of enzyme production was observed.

Table 4

| Surfactant | Optimum Conc. of Surfactant g/Liter | Extracellular Cholesterol Oxidase U./Liter |
| --- | --- | --- |
| S-1 | 10.0 | 4.4 |
| S-2 | 1.0 | 3.7 |
| S-4 | 5.0 | 9.8 |
| S-5 | 1.0 | 3.1 |
| S-6 | 5.0 | 4.6 |
| S-7 | 5.0 | 17.8 |
| S-8 | 1.0 | 4.5 |
| S-3 | 5.0 | 9.1 |
| No surfactant | — | 1.6 |

EXAMPLE 4

Effect of other Surfactants

Surfactants S-9, S-10, S-11, S-12, S-13 and S-14 - all of which contain alkyl phenol groups were tested for their ability to improve the yield of extracellular cholesterol oxidase. These compounds were tested in Erlenmeyer flasks at three concentration levels (0.05, 0.5 and 5.0 g/liter of medium) according to the procedure of Example 3. The optimum concentration for each surfactant and the amount of extracellular cholesterol oxidase produced are shown in Table 5.

Table 5

| Surfactant | Optimum Conc. of Surfactant g/Liter | Extracellular Cholesterol Oxidase U./Liter |
| --- | --- | --- |
| S-9 | 0.5 | 5.2 |
| S-10 | 0.5 | 3.9 |
| S-11 | 0.5 | 4.0 |
| S-12 | 0.5 | 6.8 |
| S-13 | 0.05 | 4.9 |
| S-14 | 0.05 | 2.4 |

Table 5-continued

| Surfactant | Optimum Conc. of Surfactant g/Liter | Extracellular Cholesterol Oxidase U./Liter |
|---|---|---|
| S-3 | 5.0 | 6.0 |
| No surfactant | — | 3.0 |

S-14 inhibited the production of the enzyme. The yields of cholesterol oxidase with S-10 and S-11 were slightly better than that observed in the medium without any detergent. The production of the extracellular enzyme was significantly improved in the presence of S-9, S-12 and S-13. The levels of cholesterol oxidase obtained with these three surfactants were comparable to those obtained with S-3. The concentrations of these surfactants, optimum for the production of cholesterol oxidase were 1 – 2 orders of magnitude lower than the optimum concentration (5 g/liter) of S-3. These surfactants at concentrations above about 0.5 g per liter inhibited the growth of *Nocardia cholesterolicum*.

EXAMPLE 5

A 150 liter fermenter containing 75 liters of sterilized modified S-3 medium is inoculated with 6 liters of 19 hour old culture of *Nocardia cholesterolicum*. This inoculum is grown as described above. The medium is agitated and aerated vigorously for 24 hours, preferably at a stirring speed of 250 RPM and an air flow rate of 0.6 V.V.M. (volume of air/volume of medium/ minute). The fermentation temperture is 30° C. At the end of 24 hours the cells are removed by centrifugation in a refrigerated continuous centrifuge. The centrifuged broth contains the extracellular cholesterol oxidase.

EXAMPLE 6

Effect of Culture

Various strains known to produce cholesterol oxidase were selected from an available culture collection. The strains were grown in S-3 medium and the cholesterol oxidase produced at 24, 48 and 72 hours was measured. Table 6 shows the maximum yield obtained.

Table 6

Production of Cholesterol Oxidase in S-3 Medium

| Strain | Cholesterol Oxidase [a] | | |
|---|---|---|---|
| | Extra-cellular | Intra-cellular | U/liter Total |
| *Arthrobacter crystallopoites* | 0.9 | —[b] | —[b] |
| *Arthrobacter* strain NP | 0.4 | —[b] | —[b] |
| *Mycobacterium* strain MA-7 | 0.6 | 0.0 | 0.6 |
| *Mycobacterium* strain E-16 | 1.7 | 0.0 | 1.7 |
| *Mycobacterium rhodochrous* | 1.1 | 0.0 | 1.1 |
| *Corynebacterium* species | 4.0 | 0.0 | 4.0 |
| *Nocardia cholesterolicum*-smooth | 20.3 | 12.4 | 32.7 |
| Nocardia cholesterolicum-rough | 16.5 | 6.7 | 23.2 |

[a]The figures represent the maximum production.
[b]Not assayed.

EXAMPLE 7

Effect of Antifoam Polyglycol P-2000

Since the addition of a surfactant, such as for example S-3, is crucial to the production of extracellular cholesterol oxidase, it was necessary to find means to control the excessive foaming owing to such addition. For this purpose, various concentrations of antifoam Polyglycol P-2000 were studied. The results show that there is a slight increase in the amounts of the extracellular and total cholesterol oxidase with the increase in the concentration of Polyglycol P-2000 up to 0.05 percent. In this concentration range (up to 0.05 percent), about 60 percent of the total enzyme was present extracellularly. Further increase in the concentration of the antifoam caused inhibition of the enzyme synthesis and shifted the distribution of the enzyme in favor of the intracellular enzyme. Studies in a 150-liter fermenter showed that 0.03 percent Polyglycol P-2000 was adequate in controlling foaming owing to the presence of surfactant S-3 in the medium.

EXAMPLE 8

Effect of Cholesterol

The effect of the amount of cholesterol present in the medium was studied by measuring the amount of enzyme produced with increasing concentration of cholesterol. The results demonstrated a 13-fold increase in the level of cholesterol oxidase produced as the concentration of cholesterol was changed from 0 to 0.5%.

EXAMPLE 9

Effect of Inositol

The effect of inositol on the production of enzyme was examined, and it was found that inositol inhibited the production of enzyme.

In view of the 3-fold increase in enzyme production realized without inositol, the experiments described in Examples 10–12 were performed utilizing a second modified S-3 nutrient medium as described below:

| Modified S-3 Medium #2 | |
|---|---|
| Nutrient Broth | 8.0 g |
| S-3 | 5.0 g |
| Yeast extract | 1.0 g |
| Cholesterol | 1.0 g |
| Distilled water | to 1 liger |

EXAMPLE 10

Testing of Other Steroids and Cholesterol Esters as Inducers of Cholesterol Oxidase a. A number of steroids were tested for their ability to induce cholesterol oxidase. As shown in Table 7, the effectiveness of different steroids in inducing the enzyme varies markedly. Studies were made in 250 ml Erlenmeyer flasks containing 25 ml of Modified S-3 Medium 2 as described above. One gram of the steroid to be tested was added per liter instead of cholesterol. In this experiment, cholesterol induced an extracellular enzyme activity of 14.7 U per liter. Addition of ground mixed soy steroids to the medium resulted in the production of the enzyme, 65% of that induced by cholesterol. $\beta$-Sitosterol and $5\alpha$-cholestan-$3\beta$-ol induced enzyme titres which were 65% and 59% of those induced with cholesterol.

Table 7

Effectiveness of Other Steroids as Inducers of Cholesterol Oxidase

| | Extracellular Activity (U/Liter) | Enzyme Activity % of Control[b] |
|---|---|---|
| Cholesterol | 14.7 | 100 |
| $\beta$-Sitosterol | 9.54 | 65 |
| Ground Mixed Soy Sterols | 9.99 | 68 |
| $5\alpha$Cholestan-$3\beta$-ol | 8.70 | 59 |
| Cholest-4-en-3-one | 6.27 | 43 |
| Mixed Soy Steryl-2-Carbamato Glutaric Acid Potassium Salt | 5.03 | 34 |

Table 7-continued
Effectiveness of Other Steroids as Inducers of Cholesterol Oxidase

| | Extracellular Activity (U/Liter) | Enzyme Activity % of Control[b] |
|---|---|---|
| 7-Dehydrocholesterol | 2.19 | 14 |

[a] Concentration of the sterols tested was 0.1%
[b] The control medium contained cholesterol as the inducer.

b. A total of 12 cholesterol esters were studied for their ability to induce cholesterol oxidase. These were tested in the same manner as the steroids. Cholesterol in the Modified, S-3 Medium #2 described above was substituted with the cholesterol ester to be investigated. Four of these 12 esters of cholesterol studied, namely, linoleate, oleate, hexanoate and propionate, induced a level of cholesterol oxidase comparable to that obtained with cholesterol in a similar medium (Table 8). Cholesteryl butyrate, cholesteryl decanoate and cholesteryl linolenate were moderately successful in inducing the enzyme. The remaining esters induced cholesterol oxidase to less than 50% of the control. Effectiveness of the esters with aromatic sidechains was even lower.

Table 8
Effectiveness of Cholesterol Esters as Inducers of Cholesterol Oxidase

| Cholesterol Ester[b] | Concentration (m moles) | Enzyme Activity % of Control[a] |
|---|---|---|
| Cholesterol | 2.6 | 100.0 |
| Cholesteryl Propionate | 2.3 | 79.7 |
| Cholesteryl Butyrate | 2.2 | 64.1 |
| Cholesteryl Hexanoate | 2.1 | 99.7 |
| Cholesteryl Benzoate | 2.0 | 45.0 |
| Cholesteryl p-Nitrobenzoate | 1.9 | 13.6 |
| Cholesteryl Decanoate | 1.9 | 63.0 |
| Cholesteryl Laurate | 1.8 | 54.2 |
| Cholesteryl Myristate | 1.7 | 49.9 |
| Cholesteryl Palmitate | 1.6 | 41.3 |
| Cholesteryl Oleate | 1.5 | 86.4 |
| Cholesteryl Linoleate | 1.5 | 112.0 |
| Cholesteryl Linolenate | 1.6 | 64.6 |

[a] The control medium contained cholesterol as the inducer.
[b] The concentration of the esters was 0.1%

EXAMPLE 11
Effect of Yeast Extract

Omission of yeast extract from the Modified S-3 Medium 2 as described above reduced the levels of the extracellular enzyme by 50% (Table 9). The enzyme synthesis increased with increasing concentrations of yeast extract up to 0.15%. There was no further increase in the production of the enzyme with concentrations of yeast extract higher than 0.15%. On the contrary, there was repression of the enzyme in the medium with 1.0% yeast extract. The proportion of the enzyme released decreased from 81% to 26% when the concentration of yeast extract was varied from 0.0% to 1.0%.

Table 9
Effect of Yeast Extract on the Production of Cholesterol Oxidase

| Concentration of Yeast Extract % | Extracellular Enzyme % of Control[a] | Proportion of Enzyme Released % |
|---|---|---|
| 0.0 | 50 | 81 |
| 0.1 | 100 | 60 |
| 0.15 | 16 | 41 |
| 0.2 | 108 | 40 |
| 0.5 | 113 | 40 |
| 1.0 | 54 | 26 |

[a] The control medium contained 0.1% yeast extract.

EXAMPLE 12
Effect of Nutrient Broth Concentration

To determine an optimum concentration of Nutrient Broth the synthesis of the enzyme was carried out in Modified S-3 Medium 2 containing varying concentrations of this main nitrogen source. Table 10 illustrates the relative enzyme yield achieved with increasing concentration of Nutrient Broth using 0.8% as a control.

Table 10
Effect of Nutrient Broth on the Production of Cholesterol Oxidase

| Concentration of Nutrient Broth % | Relative Yield Extracellular Cholesterol Oxidase |
|---|---|
| 0.0 | 18% |
| 0.2 | 50% |
| 0.4 | 80% |
| 0.8[a] | 100% |
| 1.6 | 169% |

[a] Control

EXAMPLE 13
Effect of Trace Salts

To determine the effect of trace salts the following salts were added to Modified S-3 Medium 2:

| | per liter |
|---|---|
| $MgSO_4 \cdot 7H_2O$ | 125.0 mg |
| $CaCl_2 \cdot 2H_2O$ | 0.5 mg |
| $FeSO_4 \cdot 7H_2O$ | 40.0 mg |
| $MnSO_4 \cdot H_2O$ | 8.5 mg |
| $ZnSO_4 \cdot 7H_2O$ | 0.3 mg |
| NaCl | 3.0 mg |

A two-fold increase in the production of cholesterol oxidase was noted.

The results of the above-described examples indicated that the growth medium for the production of the extracellular cholesterol oxidase from *Nocardia cholesterolicum* should contain as optimum concentrations, per liter: Nutrient Broth 8.0 g, Tween 40 5.0 g, yeast extract 1.5 g, cholesterol 5.0 g. However, scale-up studies in 150-liter fermenter indicated that cholesterol concentration should be about 1.0 g per liter. With this optimized medium up to 30 U of the extracellular cholesterol oxidase were produced.

While the invention has been described in detail with particular reference to preferred embodiments thereof, it will be understood that variations and modifications can be effected within the spirit and scope of the invention.

We claim:

1. In a method for the production of cholesterol oxidase by growing a cholesterol oxidase producing microorganism in a medium comprising a cholesterol oxidase inducer, the improvement wherein said cholesterol oxidase inducer is β-sitosterol.

2. In a method for the production of cholesterol oxidase by growing a cholesterol oxidase producing microorganism in a medium comprising a cholesterol oxidase inducer, the improvement wherein said cholesterol oxidase inducer is a ground mixed soy sterol.

* * * * *

UNITED STATES PATENT AND TRADEMARK OFFICE
CERTIFICATE OF CORRECTION

PATENT NO. : 4,072,568
DATED : February 7, 1978
INVENTOR(S) : Prakash Masurekar and Charles T. Goodhue It is certified that error appears in the above-identified patent and that said Letters Patent are hereby corrected as shown below:

Column 1, line 16, "is" should read --in--;
Column 2, line 6, "obtined" should read --obtained--;
Column 7, line 9, "cholsterol" should read --cholesterol--;
Column 11, line 9, before "act", "not" should be deleted;
Column 7, line 55, after "(dibasic)", --.-- should be inserted;
Column 11, line 36, "stain" should read --strain--;
Column 13, line 30, "temperture" should read --temperature--;
Column 14, line 37, "liger" should read --liter--
Column 14, line 59 and Column 15, line 2, "Steroids" should read --Steroids[a]-- (also omitted on page 32 of application, Table 7, line 2);
Column 15, line 66, "16" should read --116--;
Column 16, line 9, at the end of Example 11, --Riboflavin and biotin can be used to partially replace yeast extract yielding results better than those in the absence of yeast extract but less than that with optimum concentrations of yeast extract.-- should be inserted.

Signed and Sealed this

Tenth Day of October 1978

[SEAL]

Attest:

RUTH C. MASON
Attesting Officer

DONALD W. BANNER
Commissioner of Patents and Trademarks